United States Patent [19]

Convery

[11] Patent Number: 4,930,872
[45] Date of Patent: Jun. 5, 1990

[54] IMAGING WITH COMBINED ALIGNMENT FIXTURING, ILLUMINATION AND IMAGING OPTICS

[76] Inventor: Joseph J. Convery, 3182 Briar Hill, Milford, Mich. 48042

[21] Appl. No.: 280,718

[22] Filed: Dec. 6, 1988

[51] Int. Cl.$^5$ .................. G02B 27/00; G02B 23/26
[52] U.S. Cl. .................. 350/321; 350/96.26; 250/397; 356/2; 356/237; 358/139
[58] Field of Search ............ 350/321, 319, 245, 255, 350/518, 521, 522, 523, 96.25, 96.26, 96.28; 250/396 R, 397, 566, 571; 340/146.2, 501; 354/295; 356/1, 2, 3, 5, 237; 358/106, 107, 139, 159

[56] References Cited

U.S. PATENT DOCUMENTS

| | | | |
|---|---|---|---|
| 1,954,755 | 4/1934 | Heine | 88/40 |
| 2,056,421 | 10/1936 | Cooper | 88/39 |
| 2,403,892 | 7/1946 | McFarlane et al. | 88/24 |
| 2,971,093 | 2/1961 | Garbuny | 250/83.3 |
| 3,541,233 | 11/1970 | Ayres | 178/5.2 |
| 3,582,181 | 6/1971 | Manua de Chveca | 350/87 |
| 3,665,184 | 5/1972 | Schagen | 250/60 |
| 3,821,510 | 6/1974 | Muncheryan | 350/96.28 |
| 3,945,729 | 3/1976 | Rosen | 356/5 |
| 4,002,823 | 1/1977 | Van Oosterhout | 358/106 |
| 4,170,987 | 10/1979 | Anselmo et al. | 128/665 |
| 4,191,940 | 3/1980 | Poleyn et al. | 340/146.3 |
| 4,223,680 | 9/1980 | Jöbsis | 128/633 |
| 4,281,645 | 8/1981 | Jöbsis | 128/633 |
| 4,491,865 | 1/1985 | Danna et al. | 358/98 |
| 4,532,723 | 8/1985 | Kellie et al. | 356/73 |
| 4,611,888 | 9/1986 | Prehovitz et al. | 350/96.26 |
| 4,629,319 | 12/1986 | Clarke et al. | 356/237 |
| 4,659,993 | 4/1987 | Womack | 324/373 |
| 4,693,601 | 9/1987 | Dabelsteiin et al. | 356/237 |
| 4,737,650 | 4/1988 | West | 250/571 |
| 4,754,329 | 6/1988 | Lindsay et al. | 358/139 |

Primary Examiner—Bruce Y. Arnold
Assistant Examiner—Loha Ben
Attorney, Agent, or Firm—Krass & Young

[57] ABSTRACT

A hand-held device enables repeatable computerized imaging and analysis of a surface feature by combining the functions of alignment, illumination and imaging in a unitary device. The probe consists of a physical standoff having one end contacting the surface surrounding the area to be imaged. The imaging device, in the form of a lens and a charge coupled device (CCD), is mounted on the standoff at a distance from the surface area fixed by the standoff. The imaging device has its focal plane at or near the surface area to be imaged as controlled by the physical dimensions of the physical standoff. The imaging device is constructed having a depth of focus corresponding to the depth of the feature of interest on the surface area to be imaged. The illumination, in the form of a ring light disposed about the imaging device, focuses light at the focal plane of the imaging device. The device may include provision for multiple spectral imaging via multiple light sources or filtering and may also include the capability of multiple powers in the optical imaging.

17 Claims, 4 Drawing Sheets

IMAGING WITH COMBINED ALIGNMENT FIXTURING, ILLUMINATION AND IMAGING OPTICS

TECHNICAL FIELD OF THE INVENTION

The technical field of the present invention is that of imaging systems and particularly image archiving systems for the detailed dimensional analysis of surface features. This field can be called contact digital microphotography.

BACKGROUND OF THE INVENTION

It is often the case that it is desirable to take images of a surface feature under repeatable conditions. This is particularly true in applications where it is desirable to track any change in the surface feature. Currently there is no means for providing good quality moderately magnified images whose physical and optical variables are optimized and integrated in a field setting.

One application where such an imaging system would be desirable is in dermatological diagnosis of dysplastic nevi. Dysplastic nevus syndrome is a medical condition appropriate to select skin types who have a low tolerance to sunlight and a higher risk of skin cancer than the general population. Among other physical traits, an individual with dysplastic nevus syndrome typically develops a number of skin lesions (nevi), each of which may become unstable over time and must be carefully watched for signs of malignancy. These nevi typically appear on the upper body. Treatment typically requires tracking each nevus in order to determine if that nevus is undergoing physical changes in size, shape or color and may need to be excised Excision of all nevi of a patient is generally not performed, because of their great number and the increased risks associated with repeated surgeries.

In the current art, the dermatologist relies upon visual inspection of each nevus. This requires the dermatologist to remember the last state of each nevus, a difficult task due to their number, in order to detect any changes in state. Alternatively, the dermatologist could prepare a written summary of the state of each nevus or at least those of most concern. This summary would permit review of the prior state of the nevus. Such summaries are necessarily poor substitutes for review of the prior status of the nevus. It is also feasible to take ordinary photographs of the skin for later comparison. This technique is unsatisfactory because the physical conditions for taking such photographs cannot be easily repeated. This means that the photographs cannot be relied upon to clearly indicate change in the skin condition rather than change in the lighting, angle or the like when the photograph was exposed.

There are other fields where repeatable images of surface features would be helpful Quality control of industrial finishing, such as painting, would also benefit from the capability of such measurements. The results of changes in the parameters of the finishing operation could be more readily determined if images of the finished products could be compared without worry that change conditions of measurement create inconsequential differences.

It is therefore a need in the art to be able to form images of surfaces under reliably repeatable conditions in the field whose physical and optical variables have been optimized and of suitable repeatability for submission to, and analysis by, a computer.

SUMMARY OF THE INVENTION

The present invention is a unitary structure imaging system for producing a magnified electronic image of a region of a surface in a reliably repeatable manner. The imaging system includes a physical standoff structure, a source of illumination, an optical system and a camera. The physical standoff structure has one end for contacting the surface surrounding the region to be imaged. This provides a fixed physical relation between the other parts of the apparatus and the surface to be imaged. The source of illumination has a predetermined spectrum and is disposed to uniformly illuminate the particular portion of the surface to be imaged. The optical system focuses an image of objects located at a predetermined objective plane on a focal plane. The illumination source has been designed to provide maximum levels of illumination with minimal variances in illumination distribution at the objective plane. The objective plane is fixed relative to the surface to be imaged by the physical standoff structure. A television camera is disposed at the focal plane of the optical system and forms an electronic image of the surface. The unitary structure is constructed to be hand-held and capable of being brought by hand to the surface to be imaged.

The various structures of the imaging system are interrelated to provide a repeatable image of the surface at levels of magnification appropriate to the application. The physical standoff structure ensures that the optical system and camera are always in the same relationship to the surface. Likewise, the source of illumination is always in the same relationship to the surface, as set by the physical standoff structure, to provide optimal illumination for imaging.

Numerous refinements of this device are feasible. For medical applications a disposable cap is mounted on the distal end of the physical standoff structure. A new disposable cap is employed for each new patient to prevent cross contamination. A portion of the disposable cap may be in the field of view of the imaging system. The disposable cap has an opening with a size selected with respect to the compressibility of the region of the surface to be imaged to minimize crowning on particularly small targets. Because the optical system focal length may vary somewhat upon construction, the physical standoff structure includes an adjustment device for compensating for the variability of the focal length during manufacture. The imaging system may also include an operator actuatable switch to acquire an image. The source of illumination is preferably a ring light concentric with and perpendicular to the optical system axis. This ring light preferably consists of a remote electric lamp and a plurality of optic fibers. As a further refinement, a sampling fiber bundle of fibers randomly selected from among the optic fiber bundle is separated. This sampling bundle is connected to a photodetector circuit to monitor the light output from the lamp source as received by the optic fiber bundle.

BRIEF DESCRIPTION OF THE DRAWINGS

These and other objects and aspects of the present invention will become clear from the following description of the invention taken in conjunction with the drawings, in which.

DETAILED DESCRIPTION OF THE PREFERRED EMBODIMENT

The description of the invention appearing below details the features of the preferred embodiment of the present invention. In accordance with the preferred embodiment, the present invention is employed to make historical record of one or more nevi on the surface of a person's skin. As mentioned above, this historical record establishes a baseline image record of an individual nevus. Subsequent re-inspections of the same nevus enables the treating physician to determine if the nevus is undergoing any change in size, shape or color. This image archiving will permit the treating physician to determine which therapy is most effective for a particular nevus. Thus better individualized treatment is possible.

Figure 1:
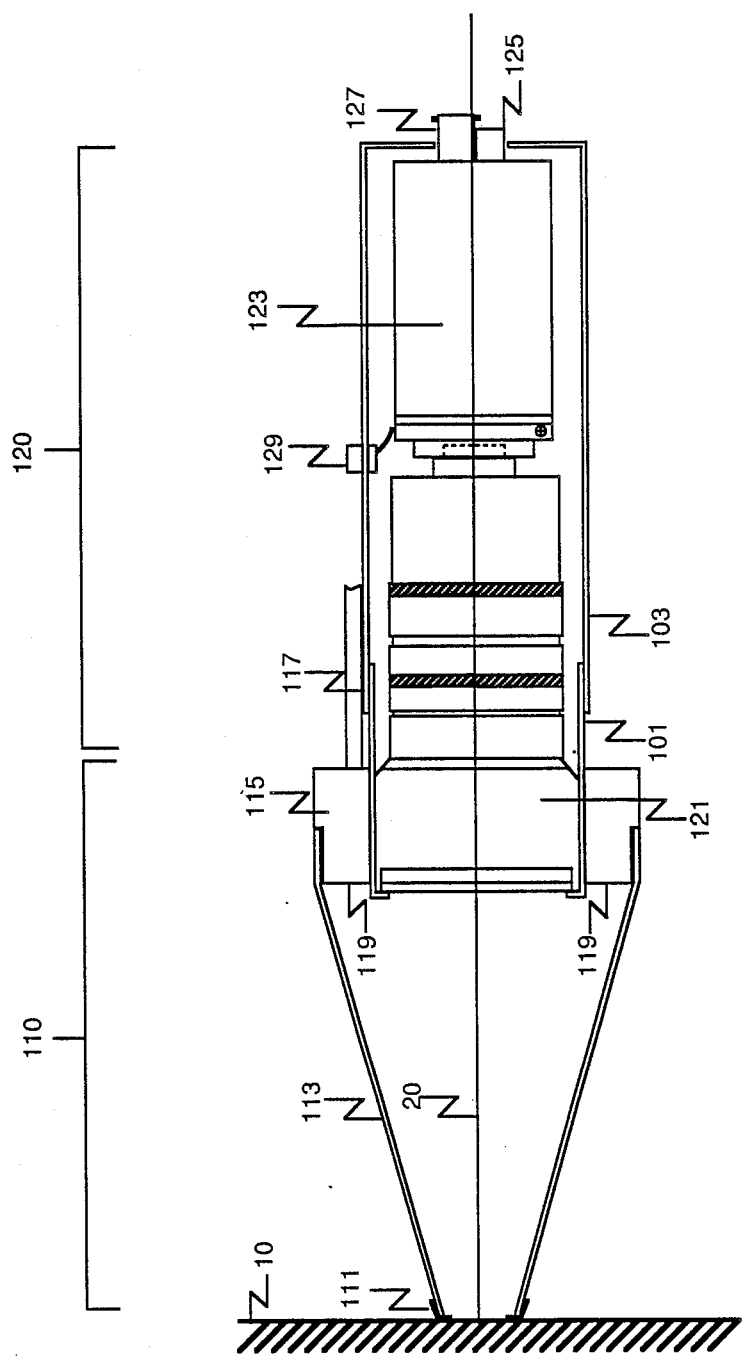
FIG. 1 illustrates a sectional view of the combined standoff, illumination and optics of the imaging system in accordance with the preferred embodiment of the present invention.

FIG. 1 illustrates in cross-sectional form the imaging system in accordance with the preferred embodiment of the present invention. Imaging system 100 is constructed of a size to be hand held and consists of two main sections: physical standoff and illumination section 110; and optics/camera section 120. Physical standoff and illumination section 110 is coupled to optics/camera section 120 via case part 101 having a threaded outside diameter for mating with the threaded inside diameter of case part 103. The imaging system 100 is employed for imaging surface features of interest on surface 10. In accordance with the present invention, imaging system 100 is cylindrically symmetrical about prime axis 20.

Physical standoff and illumination section 110 includes a threaded distal ring 111 and a connecting proximal ring 115 which includes a ring light 119. The conical section 113 separates the distal ring 111 and the proximal ring 115 by a predetermined distance related to the focal length of lens system 121. Both distal ring 111 and proximal ring 115 are preferably symmetrical about and perpendicular to prime axis 20. The surface 10 is viewed through the center of distal ring 111 from the optics section through the center of proximal ring 115. Conical section 113 preferably includes a texturized coating or is painted in black. This surface coating is provided to prevent unwanted reflections from conical section 113 from entering the optics/camera section 120. This coating preferably absorbs all wavelengths in the visible spectrum. As an alternative, conical section 113 need only absorb light in the wavelength or wavelengths produced by ring light 119.

Physical standoff and illumination section 110 also includes fiber optic bundle 117 and ring light 119. Fiber optic bundle 117 couples light from a lamp (not shown in FIG. 1, see lamp 130 FIG. 6) via a plurality of optic fibers to ring light 119. The ends of the optic fibers are disposed in a fixed distribution pattern and at a fixed exit angle in a ring about the opening in proximal ring 115. Each optic fiber emits light coupled from the lamp. The ends of these optic fibers are directed so that the optimal illumination appears at surface 10 when distal ring 111 is abutting surface 10. Ring light 119 serves to illuminate the feature of interest on the surface 10 in a controlled and repeatable manner. The spectrum of light emitted by the lamp and produced by ring light 119 is selected with due regard to the feature of interest on surface 10.

Optics/camera section 120 includes an optical system 121 disposed in a case part 103. The optical system 121 is preferably a compound lens system. The purpose of optical system 121 is to focus an image of the feature of interest on surface 10 on the focal plane of television camera 123. Optical system 121 is of the type ordinarily employed in 16 millimeter cameras. Optical system 121 is disposed so that its optical axis coincides with the prime axis 20. In accordance with the preferred embodiment of the present invention, optical system 121 provides a magnification of a factor of approximately 20.

The case part 103 serves to cover and protect optical system 121 and camera 123, and to provide a convenient hand hold for holding imaging system 100. A momentary contact push button switch 129 may be mounted on case part 103. Switch 129 enables the operator to indicate when imaging system 100 is aligned with respect to surface 10 to provide a valid image. The use of this signal will be further described below.

Optics/camera section 120 includes a video camera 123, input connector 125 and output connector 127. Video camera 123 mates with lens system 121 in order to produce an electronic signal corresponding to the magnified image of the feature of interest. In accordance with the preferred embodiment of the present invention, camera 123 includes a charge coupled device as its imaging device. The charge coupled device is driven for read-out in accordance with scan signals received on input connector 125. This device then produces an analog video signal on the output connector 127 in accordance with the light received. Output connector 127 may also permit transmission of other signals such as the state of switch 129.

Camera 123 has an illumination sensitivity which is optimized with respect to the particular wavelength or wavelengths of light produced by ring light 119. This illumination is selected with due regard to the expected feature to be imaged in order to insure that a stable image is available for visual or computer analysis.

Imaging system 100 is constructed to optimize the production of an image of an object at a particular location. This particular location is at the distal end of distal ring 111. The illumination from ring light 119 is projected to uniformly illuminate the surface feature of interest on the surface 10 with light of appropriate wavelength or wavelengths to enable a proper image of this feature. In accordance with the preferred embodiment in which the imaging system 100 is employed to take images of skin nevi, the illumination from ring light 119 is in the visible spectrum. Conical section 113 serves to position optics/camera section 120 at the optimum distance from surface 10 for the proper focus for camera 123. The particular magnification desired is selected with regard to the type of surface feature of interest. In the preferred embodiment in which the surface feature of interest is a skin nevus, the magnification is set at approximately 20. The imaging device of camera 123 is then mounted on the focal plane of lens system 121. This optical combination then determines the optimum distance from lens system 121 to the feature of interest to insure prime focus of features at distal ring 111. Conical section 113 is then constructed to provide this distance between the surface 10 and lens system 121.

Optical system 100 can be employed to take repeatable images of the same surface feature. This is possible because the construction of conical section 113 enables the lens system 121 and camera 123 to be placed in a repeatable relationship to the surface. The feature of interest is placed within the hole of distal ring 111 and distal ring 111 is abutted to the surface 10. This placement automatically places the lens system 121 and camera 123 in the optimal location for imaging the feature of interest on surface 10. Because the focus dimensions of imaging system 100 are predetermined relative to the distal ring 111 by conical section 113, the position relative to the surface 10 ca be reliably repeated. This repeatability permits a time history of the feature of interest under the same conditions to be acquired. Thus the differences in the historical images are due to differences in the feature of interest and not to differences in the measurement conditions.

Figure 2:
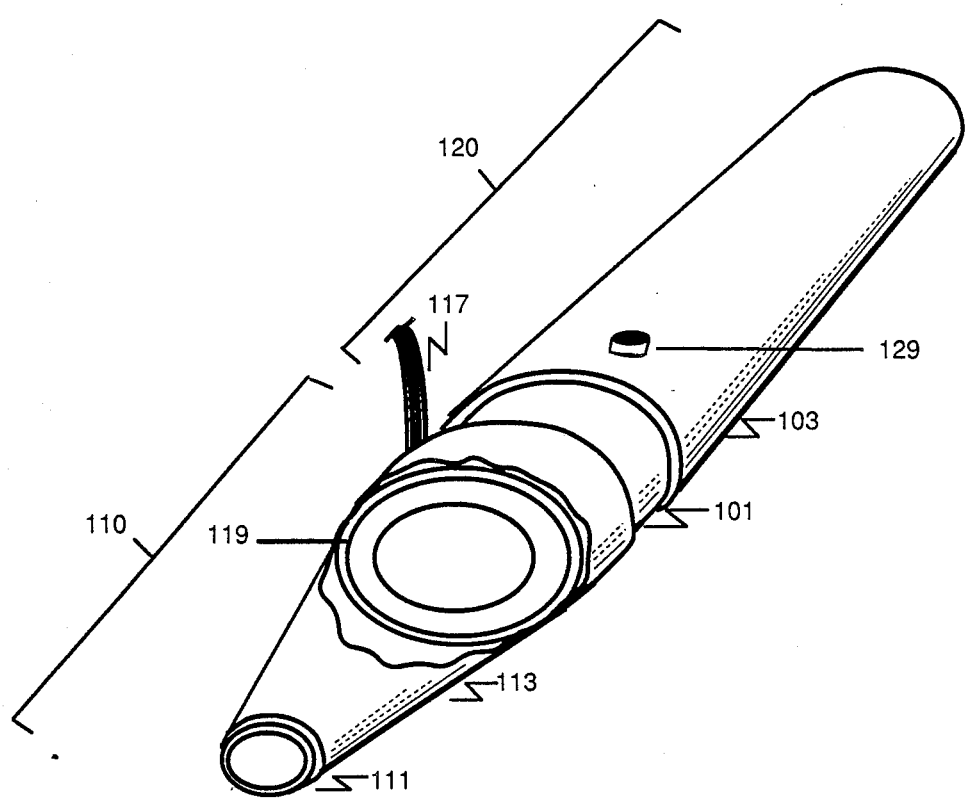
FIG. 2 illustrates a perspective view of the imaging system illustrated in FIG. 1.

FIG. 2 illustrates imaging system 100 in perspective, partial cut-away form. FIG. 2 provides a better view of ring light 119 within the cut-away section of conical section 113. In addition the opening in distal ring 111 is illustrated in FIG. 2.

Figure 3:
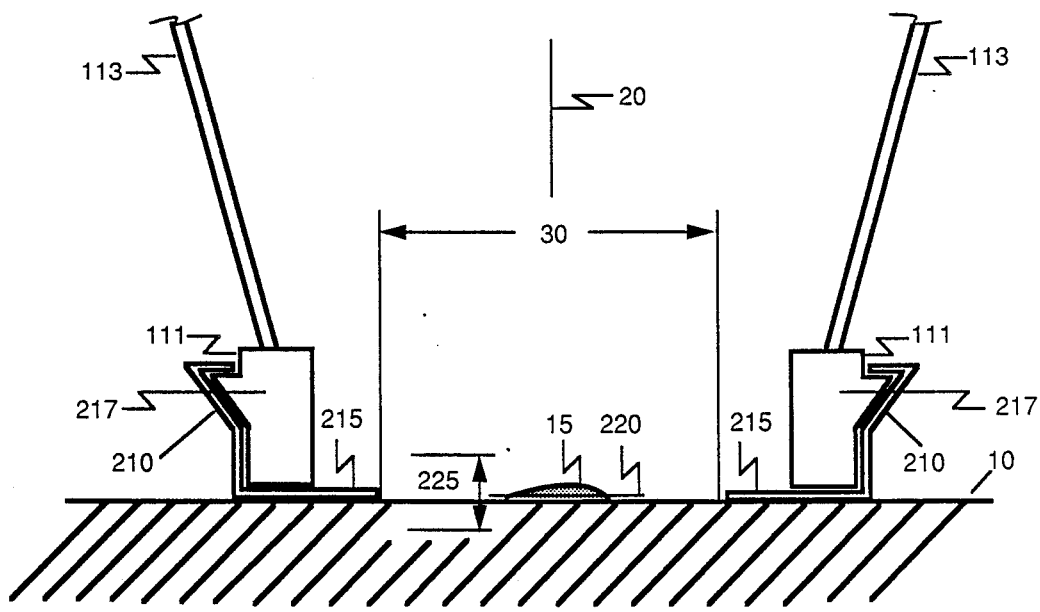
FIG. 3 illustrates in detail the distal ring of the imaging system in accordance with the preferred embodiment of the present invention showing a disposable end cap.

FIG. 3 is a detailed sectional view of distal ring 111. Distal ring 111 is attached to the far end of conical section 113. Distal cap 210 is mounted on distal ring 111 by a slip fit and locked by means of notch 217. In the preferred embodiment, imaging system 100 is employed to form images of skin nevi. Distal cap 210 is provided to prevent cross contamination between different persons. Distal cap 210 is preferably formed of an inexpensive plastic which is discarded after use on each patient. This permits a new distal cap 210 to be employed for each new patient.

Distal cap 210 includes a section 215 which projects into the hole in distal ring 111. The surface 10, the skin of a person in the preferred embodiment, has a known compressibility. This known compressibility provides a slight crowning effect such as illustrated in FIG. 3. The diameter of the hole of projecting section 215 is selected so that any slight crowning is minimized by increasing the surface area of imaging system 100 as it contacts surface 10. The inner portion of projecting section 215 is outside the field of view 30 of camera 123. This prevents the reflectivity of projecting section 215 from interfering with computer analysis of the image captured by imaging system 100.

Figure 4:
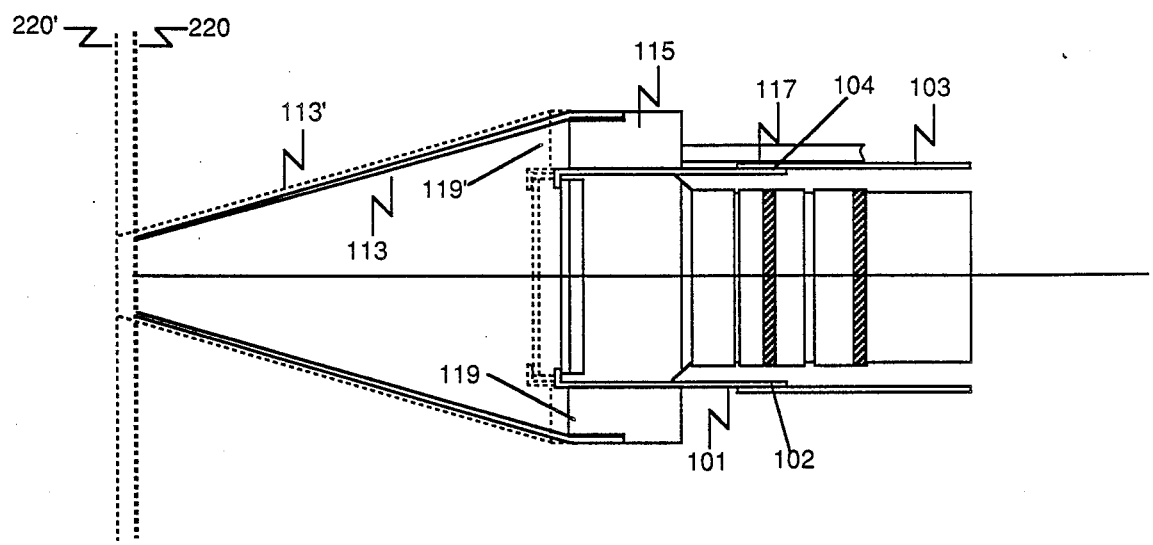
FIG. 4 illustrates the preferred embodiment for adjustment of the focus of the imaging system of the present invention to compensate for variability in the focal length of the optical system.

FIG. 4, taken together with FIG. 3, illustrates a manner of adjustment for variability in focal length of optical system 121. Case part 101 includes an outer threaded section 102. This outer threaded section 102 mates with an inner threaded section 104 of case part 103. The degree of overlap of case parts 101 and 103 is controlled by rotation of these sections relative to each other with mating threaded sections 102 and 104. It is believed that there will be inevitable focal length errors in construction of lens system 121 which will lead to variations in the location of the objective plane. Because imaging system 100 is designed to provide best performance at a fixed objective plane, some manner of correction is desirable.

As illustrated in FIG. 3, the feature of interest on the surface 10 is a skin nevus 15. The ideal location for the objective plane is at plane 220 at the surface 10. In order to correct for any errors in construction of lens system 121 a calibration is made during manufacture. Imaging system 100 is employed to view a test object simulating the feature of interest. The case parts 101 and 103 are rotated relative to each other to provide optimal focus at plane 220. The case parts 101 and 103 are then permanently locked in this position. In accordance with the preferred embodiment of the present invention, permanent locking is achieved via glue between threaded portions 102 and 104. The glue is placed between threaded portions 102 and 104 prior to calibration. The calibration is performed before this glue is set. Thereafter the position of case parts 101 and 103 is not disturbed until the glue sets. Other means of locking these parts in the desired position, such as a set screw, are also feasible.

In addition to being constructed with the objective plane at plane 220, lens system in conjunction with camera 123 preferably has a depth of field 225 closely related to the depth nevus 15. This is achieved by providing a proper aperture within lens system 121.

Figure 5:
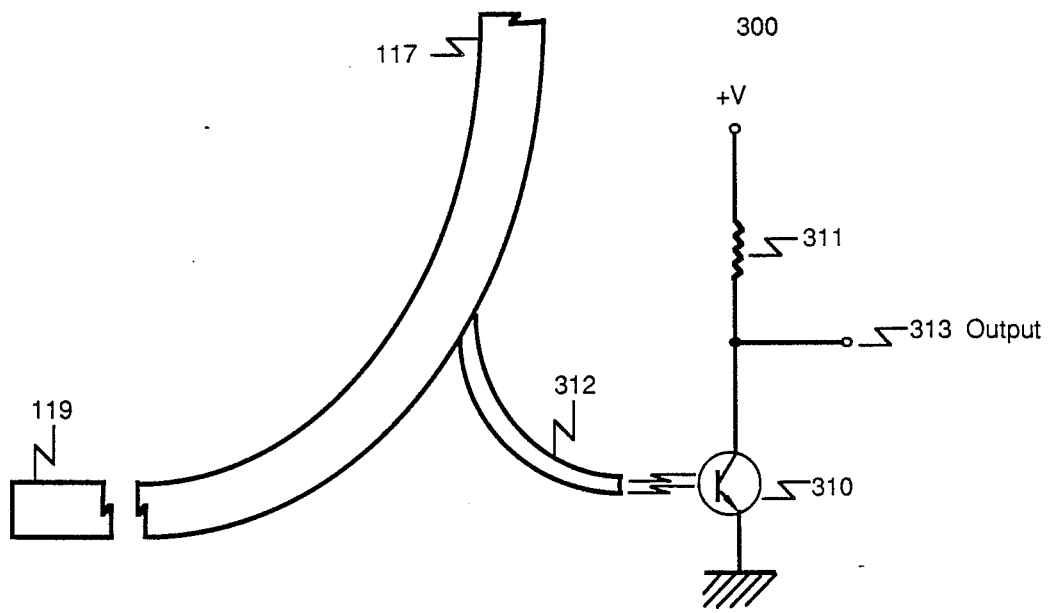
FIG. 5 illustrates in schematic diagram form a circuit for detecting the illumination brightness.

FIG. 5 illustrates a sensing circuit 300 which enables monitoring of the brightness of illumination. FIG. 5 illustrates fiber optic bundle 117. Most of the optic fibers in fiber optic bundle 117 are routed to ring light 119. A randomly selected set of optic fibers 312 is employed in the monitoring of the level of light in fiber optic bundle 117. Light from optic fibers 312 is coupled to phototransistor 310. Phototransistor 310 has a conductivity which is dependent upon the amount of light received. The intensity of light from lamp 130 thus controls the conductivity of phototransistor 310. The amount of current drawn through resistor 311 varies with the conductivity of phototransistor 310. Thus the output terminal 313 has a voltage dependent upon light intensity. This signal can be supplied to camera encoder and control circuit 421 (FIG. 6) to enable digitization based upon the level of illumination.

Figure 6:
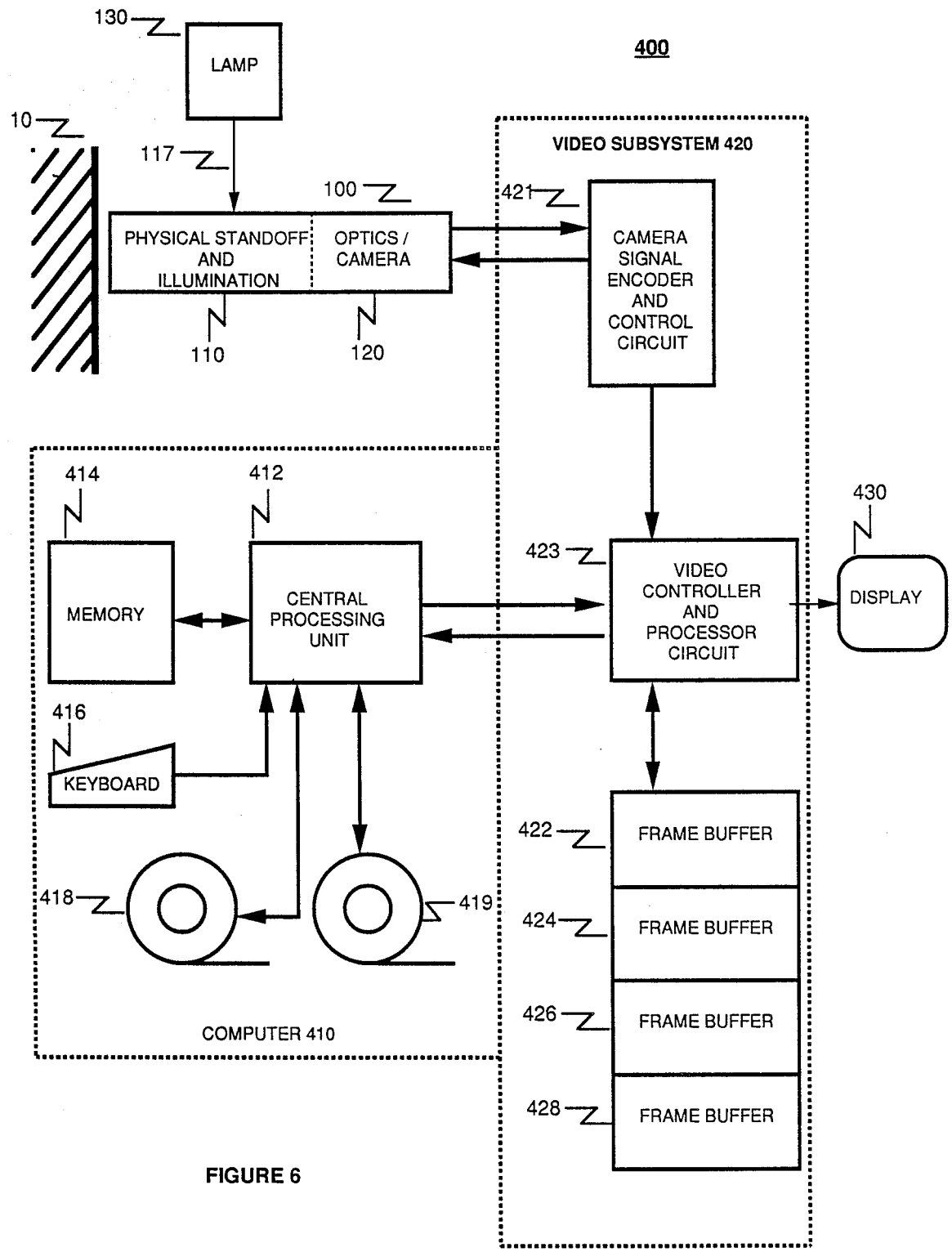
FIG. 6 illustrates in block diagram form the combination of the imaging system and the computer workstation in accordance with the preferred embodiment of the present invention.

FIG. 6 illustrates in block diagram form the computer workstation 400 coupled to imaging system 100 in accordance with the preferred embodiment of the present invention. As illustrated in FIG. 6, the imaging system 100 includes: physical standoff and illumination section 110; optics/camera section 120; and lamp 130. These structures are illustrated in abstract form in FIG. 6. The details of the preferred embodiment of imaging system 100 are better illustrated in FIGS. 1 and 2.

The computer workstation 400 includes: computer 410; and video subsystem 420. In accordance with the preferred embodiment of the present invention, computer 410 is a desk top personal computer. Such computers are available from a number of manufacturers. This computer preferably has the computing power of the class of the IBM PC AT, Sun Microsystems 350 or Apple MacIntosh II. Video subsystem 420 is preferably a plug-in board mounted within the cabinet of computer 410 in a manner known in the art. In particular, at least for this application, video subsystem 420 preferably interfaces with computer 410 to display both the graphic images of this application as well as the normal video display of computer 410. Alternatively, video subsystem 420 and display 430 can be independent of the normal video display of compute 410.

Computer 410 is constructed in accordance with the prior art. As illustrated in Figure 6, computer 410 consists of: central processing unit 412; memory 414; keyboard 416; Winchester disk memory 418; and read/write removable optical disk memory 419. Central processing unit 412 operates on programs which are stored in memory 414. Memory 414 includes some read only memory for basic functions such as initialization of computer 410 and basic input and output functions. Memory 414 also includes volatile random access read/write memory which can be used for storage of operating program and data. Programs are permanently stored in Winchester disk memory 418. In response to user commands entered via keyboard 416, central processing unit 412 recalls a selected program from Winchester disk memory 418 and loads it into memory 414. Central processing unit 412 is thereafter responsive to program instructions stored in memory 414. In accordance with the preferred embodiment of the present invention, historical image data together with accompanying morphological characteristic data is stored in read/write removable optical disk memory 419. This technique is employed because the amount of this data makes the use of so-called "floppy" disks or a Winchester hard disk drive unwieldy.

Video subsystem 420 is coupled to imaging system 100, computer 410 and display 430. Video subsystem 420 receives the electronic image data from imaging system 100, commands and data from central processing unit 412 and generates the proper signals for control of display 430. Video subsystem 420 includes: camera signal encoder and control circuit 421; video controller and processor circuit 423; and a plurality of frame buffer memories frame buffer 422, frame buffer 424, frame buffer 426 and frame buffer 428. Video controller and processor circuit 423 also preferably includes the capability of performing operations on the image data in a manner that will be detailed below.

Camera signal encoder and control circuit 421 interfaces with imaging system 100. Camera signal encoder and control circuit 421 produces all the signals needed for proper operation of camera 123. In the preferred embodiment, camera 123 includes a charge coupled device. Camera signal encoder and control circuit 421 provides the necessary timing and control signals to read out illumination information captured in individual cells of this charge coupled device in accordance with a selected scan system. This data is preferably read out as analog video data of the raster scan type. Camera signal encoder and control circuit 421 converts this analog data into corresponding digital data in synchronism with its receipt. This provides a steady stream of digital image data to video controller and processor circuit 423. Camera signal encoder and control circuit 421 may also encode other data generated by imaging system 100 (such as an image valid input or alignment data) in a manner which will be further detailed below.

Video controller and processor circuit 423 provides a clearing house for the functions of the video subsystem 420. Video controller and processor circuit 423 operates in accordance with the video protocol of computer 410. If computer 410 supports more than one video protocol, then video controller and processor circuit 423 preferably operates in accordance with the supported video protocol which provides the best graphic images. Video controller and processor circuit 423 operates in conjunction with the various frame buffers 422 to 428 to provide the required video signal to display 430. Display 430 is preferably a color cathode ray tube. Video controller and processor circuit 423 operates as a slave to central processing unit 412 in control of the video display.

A typical operation of the present invention requires video controller and processor circuit 423 to operate on several independently timed operations. One operation of the present invention involves the simultaneous display of a selected historical image and a real time image from imaging system 100 on the same screen. Such an operation would be accomplished as follows.

The historical image is located within optical disk memory, 419 by central processing unit 412. Central processing unit 412 directs the recall of the data of this historical image. This data is then supplied to video controller and processor circuit 423. Video controller and processor circuit 423 stores this historical image data in frame buffer 422. The memory location within frame buffer 422 where data for each picture element (pixel) of the historical image is stored corresponds to its position within the historical image. Video controller 423 is now ready to provide the simultaneous display required.

The real time image data from imaging system 100 is received via camera signal encoder and control circuit 421. Video controller and processor circuit 423 stores this data in frame buffer 424 with data for each pixel stored in a location corresponding to its location within the real time image. When frame buffer is full of data, that is when a full frame of real time data is stored, video controller and processor circuit 423 begins to store received real time image data in frame buffer 426. As in the previous case, data for each pixel of the real time image is stored in a memory location within frame buffer 426 corresponding to its location within the real time image. The process repeats when frame buffer 426 is full so that frame buffer 424 and frame buffer 426 are alternately loaded. This storage process takes place in synchronism with the scan rate of camera 123 set by camera signal encoder and control circuit 421.

Simultaneously with this process of receiving and storing data from image system 100, video controller and processor circuit 423 controls the display on display 430. In this example the display desired includes a side-by-side representation of the historical image and the real time image. Video controller and processor circuit 423 controls recall of individual pixel data from frame buffer 422 and the one of frame buffers 424 and 426 not currently receiving data from image system 100. The timing of this operation would in general be independent of the timing of the scan of the imaging system 100. This timing is determined by the scan system employed by display 430.

In conjunction with this operation, video controller and processor circuit 423 must also present signals to display 430 in the form that display 430 is designed to receive. This may involve conversion of digital data recalled from one of the frame buffers 422 to 428 into analog form. It may also involve generation of separate red, green and blue drive signals or generation of a composite video signal with color phase information and synchronization and blanking information. Regardless of the type of signal required by display 430, video controller and processor circuit 423 converts the digital pixel data from the frame buffers 422 to 428 into the appropriate signal for display on display 430. This process is well known in the art and will not be discussed further.

It is expected that in some portions of a single frame would include a portion of a line from the historical image and another portion of the line from the real time image. In addition, these two images may not fill the screen. Additional display of text identifying the historical image, and user instructions is contemplated. This data would be provided by central processing unit 412 and stored within frame buffer 428. In accordance with instructions from central processing unit 412, video controller and processor circuit 423 would assemble the individual lines of the display by recall of the necessary data from the various frame buffers 422 to 428. This process is known in the art and would typically involve the use of plural address registers for corresponding frame buffers which are updated to refer to the next memory location for recall of data from that frame buffer.

Note that whenever one of frame buffer 424 or 426 is full and data from imaging system 100 is directed to the other frame buffer, it is necessary to also switch the source of the data displayed on display 430. Typically this task is achieved by changing a single higher order bit in one of the address registers. This process of alternately filling one frame buffer and displaying from the other is known in the art. This process eliminates the contention for memory such as when the video controller and processor circuit 423 must simultaneously store received real image data in a memory location and recall this data for display. In addition it permits the reconciliation of possibly incompatible scan systems of the camera 123 and the display 430.

The present invention also contemplates the acquiring of real time data for analysis and storage. This capture process takes place by interrupting the storage of the stream of real time image data from imaging system 100. Upon receipt of an acquire signal, which may be generated by acquire push button 129, video controller and processor circuit 423 no longer stores received real time data in one of the frame buffers 424 and 426. This can take place immediately by stopping the storage of such data upon receipt of the acquire signal, or it could take place at the end of the current frame. This data is now "acquired" by being stored in one of the frame buffers 424 and 426. This data could be analyzed, compared with the historical data in frame buffer 422 or it could be supplied to central processing unit 412 for storage in optical disk memory 419. Any such analysis or comparison could take place in central processing unit 412, or preferably, video controller and processor circuit 423 is constructed with the capability to perform these functions under direction of central processing unit 412.

I claim:

1. A unitary structure imaging system for producing an electronic image of a region of a surface comprising:
   a physical standoff structure generally symmetrical about a primary axis including
      a distal ring disposed perpendicular to said primary axis for contacting the surface surrounding the region to be imaged, said distal ring having a distal opening permitting view of the region to be imaged along said primary axis,
      a proximal ring disposed perpendicular to said primary axis having a proximal opening permitting view of the region to be imaged along said primary axis, and
      a support structure coupled to said distal ring and said proximal ring for separating said distal ring and said proximal ring by a predetermined distance along said primary axis;
   an illuminator generating electromagnetic radiation of a predetermined spectrum disposed to uniformly illuminate said distal opening;
   an optical system disposed in said proximal opening having an optical axis coincident with said primary axis for focusing on a focal plane an image of electromagnetic radiation of said predetermined spectrum reflected from objects located at a predetermined objective plane of said optical system, said predetermined objective plane being parallel to said distal ring at a location corresponding to an expected position of the region of the surface to be imaged as determined by said predetermined distance of said support structure;
   an electronic imaging device disposed at said focal plane of said optical system responsive to electromagnetic radiation of said predetermined spectrum for generating an electronic signal corresponding to said image of electromagnetic radiation of said predetermined spectrum focused on said focal plane by said optical system, said optical system and said electronic imaging device cooperating together to produce a field of view at said predetermined objective plane concentric with said primary axis and corresponding to said distal opening.

2. The unitary structure imaging system as claimed in claim 1, further comprising:
   an operator actuatable image valid switch for receiving an operator input indicating a valid image being acquired by said electronic imaging device.

3. The unitary structure imaging system as claimed in claim 1, wherein:
   said illuminator consists of a ring light disposed on said proximal ring concentric with respect to said primary axis.

4. The unitary structure imaging system as claimed in claim 3, wherein:
   said ring light has a source consisting of an electric lamp disposed remotely from said unitary structure imaging system and a plurality of optic fibers having near ends disposed on said proximal ring concentric with respect to said primary axis for illumination of said distal opening and far ends disposed in light communication with said electric lamp, whereby light from said electric lamp is communicated via said optic fibers to illuminate said distal opening.

5. The unitary structure imaging system as claimed in claim 4, further comprising:
   at least one sampling optic fiber having a near end and a far end disposed in light communication with said electric lamp;
   a photodetector disposed to receive light from said near end of said at least one sampling optic fiber for determining intensity of electromagnetic radiation, whereby light from said electric lamp is communicated via said at least one sampling optic fiber to said photodetector for determination of illumination intensity for calibration.

6. The unitary structure imaging system as claimed in claim 1, wherein:
   said optical system consists of a lens system.

7. The unitary structure imaging system as claimed in claim 1, wherein:
said predetermined objective plane of said optical system provides prime focus of said optical system at a vertical midpoint of an expected feature of the region of the surface to be imaged.

8. The unitary structure imaging system as claimed in claim 1, wherein:
said optical system provides a magnification of approximately twenty times.

9. The unitary structure imaging system as claimed in claim 1, wherein:
said electronic imaging device consists of a charge coupled device.

10. The unitary structure imaging system as claimed in claim 1, further comprising:
an operator actuatable image valid switch for receiving an operator input indicating a valid image being acquired by said electronic imaging device;
wherein said electronic imaging device is connected to said operator actuatable image valid switch for electronically capturing an image when said operator actuatable image valid switch is actuated.

11. A unitary structure imaging system for producing an electronic image of a region of a surface, the surface having a predetermining compressibility, said imaging system comprising:
a physical standoff structure generally symmetrical about a primary axis including
a distal ring disposed perpendicular to said primary axis for contacting the surface surrounding the region to be imaged, said distal ring having a distal opening permitting view of the region to be imaged along said primary axis, the size of said distal opening being selected with respect to the predetermined compressibility of the region of the surface to be imaged to minimize crowning of the region of the surface to be imaged,
a proximal ring disposed perpendicular to said primary axis having a proximal opening permitting view of the region to be imaged along said primary axis, and
a support structure coupled to said distal ring and said proximal ring for separating said distal ring and said proximal ring by a predetermined distance along said primary axis;
an illuminator generating electromagnetic radiation of a predetermined spectrum disposed to uniformly illuminate said distal opening;
an optical system disposed in said proximal opening having an optical axis coincident with said primary axis for focusing on a focal plane an image of electromagnetic radiation of said predetermined spectrum reflected from objects located at a predetermined objective plane of said optical system, said predetermined objective plane being parallel to said distal ring at a location corresponding to an expected position of the region of the surface to be imaged as determined by said predetermined distance of said support structure, said optical system having said predetermined distance of said predetermined objective plane from said distal ring corresponding to said minimized crowning whereby said predetermined objective plane is located at the surface to be imaged having said minimized crowning;
an electronic imaging device disposed at said focal plane of said optical system responsive to electromagnetic radiation of said predetermined spectrum for generating an electronic signal corresponding to said image of electromagnetic radiation of said predetermined spectrum focused on said focal plane by said optical system, said optical system and said electronic imaging device cooperating together to produce a field of view at said predetermined objective plane concentric with said primary axis and corresponding to said distal opening.

12. A unitary structure imaging system for producing an electronic image of a region of a surface comprising:
a physical standoff structure generally symmetrical about a primary axis including
a distal ring disposed perpendicular to said primary axis for contacting the surface surrounding the region to be imaged, said distal ring having a distal opening permitting view of the region to be imaged along said primary axis,
a disposable distal cap mounted on said distal ring having a distal cap opening corresponding to said distal opening, whereby said distal cap can be mounted on said distal ring prior to producing the electronic image of the region of the surface and then discarded for preventing cross contamination between differing surfaces,
a proximal ring disposed perpendicular to said primary axis having a proximal opening permitting view of the region to be imaged along said primary axis, and
a support structure coupled to said distal ring and said proximal ring for separating said distal ring and said proximal ring by a predetermined distance along said primary axis;
an illuminator generating electromagnetic radiation of a predetermined spectrum disposed to uniformly illuminate said distal opening;
an optical system disposed in said proximal opening having an optical axis coincident with said primary axis for focusing on a focal plane an image of electromagnetic radiation of said predetermined spectrum reflected from objects located at a predetermined objective plane of said optical system, said predetermined objective plane being parallel to said distal ring at a location corresponding to an expected position of the region of the surface to be imaged as determined by said predetermined distance of said support structure; and
an electronic imaging device disposed at said focal plane of said optical system responsive to electromagnetic radiation of said predetermined spectrum for generating an electronic signal corresponding to said image of electromagnetic radiation of said predetermined spectrum focused on said focal plane by said optical system, said optical system and said electronic imaging device cooperating together to produce a field of view at said predetermining objective plane concentric with said primary axis and corresponding to said distal opening.

13. The unitary structure imaging system as claimed in claim 12, wherein the region of the surface to be imaged has a predetermined compressibility, and:
said distal cap opening of said disposable distal cap is smaller than and concentric with said distal opening whereby the size of said distal cap opening is selected with respect to the predetermined compressibility of the region of the surface to be imaged to minimize crowning of the region of the surface to be imaged; and said optical system is constructed having said predetermined distance which is also the distance of said predetermined objective plane from said proximal ring corresponding to said minimized crowning whereby said predetermined objective plane is located at the surface to be imaged having said minimized crowning.

14. A unitary structure imaging system for producing an electronic image of a region of a surface comprising:
a physical standoff structure generally symmetrical about a primary axis including
a distal ring disposed perpendicular to said primary axis for contacting the surface surrounding the region to be imaged, said distal ring having a distal opening permitting view of the region to be imaged along said primary axis,
a proximal ring disposed perpendicular to said primary axis having a proximal opening permitting view of the region to be imaged along said primary axis, and
a support structure coupled to said distal ring and said proximal ring for separating said distal ring and said proximal ring by a predetermined distance along said primary axis;
an illuminator generating electromagnetic radiation of a predetermined spectrum disposed to uniformly illuminate said distal opening;
an optical system disposed in said proximal opening having an optical axis coincident with said primary axis for focusing on a focal plane an image of electromagnetic radiation of said predetermined spectrum reflected from objects located at a predetermined objective plane of said optical system, said predetermined objective plane being parallel to said distal ring at a location corresponding to an expected position of the region of the surface to be imaged as determined by said predetermined distance of said support structure, said optical system having a focal length which is variable upon construction whereby the distance from said proximal ring to said predetermined objective plane varies upon construction;
a depth adjustment device having a depth selectable during manufacture for locating said predetermining objective plane at the expected position of the region of the surface to be imaged, thereby compensating for the variability upon construction of said focal length of said optical system; and
an electronic imaging device disposed at said focal plane of said optical system responsive to electromagnetic radiation of said predetermined spectrum for generating an electronic signal corresponding to said image of electromagnetic radiation of said predetermined spectrum focused on said focal plane by said optical system, said optical system and said electronic imaging device cooperating together to produce a field of view at said predetermined objective plane concentric with said primary axis and corresponding to said distal opening.

15. The unitary structure imaging system as claimed in claim 14, wherein:
said depth adjustment device consists of
a first case part having said physical standoff structure disposed thereon, and having an outer threaded section,
a second case part having said optical system disposed therein, having an inner threaded section for mating with said outer threaded section of said first case part, and permitting a controlled degree of overlap between said first case part and said second case part, and
a means for securing said first case part and said second case part in an overlap placing said optical system a distance for said distal ring corresponding to said focal length.

16. A unitary structure imaging system for producing an electronic image of a region of a surface comprising:
a physical standoff structure generally symmetrical about a primary axis including
a distal ring disposed perpendicular to said primary axis for contacting the surface surrounding the region to be imaged, said distal ring having a distal opening permitting view of the region to be imaged along said primary axis,
a proximal ring disposed perpendicular to said primary axis having a proximal opening permitting view of the region to be imaged along said primary axis, and
a support structure coupled to said distal ring and said proximal ring for separating said distal ring and said proximal ring by a predetermined distance along said primary axis;
an illuminator generating electromagnetic radiation of a predetermined spectrum disposed to uniformly illuminate said distal opening, said electromagnetic radiation of said predetermined spectrum being focused and uniformly distributed upon said predetermined objective plane;
an optical system disposed in said proximal opening having an optical axis coincident with said primary axis for focusing on a focal plane an image of electromagnetic radiation of said predetermined spectrum reflected from objects located at a predetermined objective plane of said optical system, said predetermined objective plane being parallel to said distal ring at a location corresponding to an expected position of the region of the surface to be imaged as determined by said predetermined distance of said support structure;
an electronic imaging device disposed at said focal plane of said optical system responsive to electromagnetic radiation of said predetermined spectrum for generating an electronic signal corresponding to said image of electromagnetic radiation of said predetermined spectrum focused on said focal plane by said optical system, said optical system and said electronic imaging device cooperating together to produce a field of view at said predetermined objective plane concentric with said primary axis and corresponding to said distal opening.

17. A unitary structure imaging system for producing an electronic image of a region of a surface comprising:
a physical standoff structure generally symmetrical about a primary axis including
a distal ring disposed perpendicular to said primary axis for contacting the surface surrounding the region to be imaged, said distal ring having a distal opening permitting view of the region to be imaged along said primary axis,
a proximal ring disposed perpendicular to said primary axis having a proximal opening permitting view of the region to be imaged along said primary axis, and
a support structure coupled to said distal ring and said proximal ring for separating said distal ring and said proximal ring by a predetermined distance along said primary axis;

an illuminator generating electromagnetic radiation of a predetermined spectrum disposed to uniformly illuminate said distal opening;

an optical system disposed in said proximal opening having an optical axis coincident with said primary axis for focusing on a focal plane an image of electromagnetic radiation of said predetermined spectrum reflected from objects located at a predetermined objective plane of said optical system, said predetermined objective plane being parallel to said distal ring at a location corresponding to an expected position of the region of the surface to be imaged as determined by said predetermined distance of said support structure, aid optical system having an aperture providing a depth of focus corresponding to a vertical dimension of an expected feature of the region of the surface to be imaged; and an electronic imaging device disposed at said focal plane of said optical system responsive to electromagnetic radiation of said predetermined spectrum for generating an electronic signal corresponding to said image of electromagnetic radiation of said predetermined spectrum focused on said focal plane by said optical system, said optical system and said electronic imaging device cooperating together to produce a field of view at said predetermined objective plane concentric with said primary axis and corresponding to said distal opening.

* * * * *

UNITED STATES PATENT AND TRADEMARK OFFICE
CERTIFICATE OF CORRECTION

PATENT NO. : 4,930,872

DATED : June 5, 1990

INVENTOR(S) : Convery

It is certified that error appears in the above-identified patent and that said Letters Patent is hereby corrected as shown below:

Column 1, line 18, "change" should be --changes--.

Column 1, line 35, "excised Excision" should be --excised. Excision--.

Column 1, line 58, "helpful Quality" should be --helpful. Quality--.

Column 4, line 45, "read-out" should be --read out--.

Column 5, line 25, "ca" should be --can--.

Column 7, line 3, "compute" should be --computer--.

Column 8, line 16, "memory, 419" should be --memory 419--.

Signed and Sealed this

Second Day of October, 1990

*Attest:*

HARRY F. MANBECK, JR.

*Attesting Officer*   *Commissioner of Patents and Trademarks*